United States Patent [19]

Steiner

[11] Patent Number: 5,512,091

[45] Date of Patent: Apr. 30, 1996

[54] ASSOCIATIVE POLYMER HYDROGELS

[76] Inventor: Carol A. Steiner, 1166 Hope St. #6, Stamford, Conn. 06907

[21] Appl. No.: 435,016

[22] Filed: May 4, 1995

Related U.S. Application Data

[63] Continuation of Ser. No. 565,704, Aug. 13, 1990.

[51] Int. Cl.$^6$ .............................. C09D 101/28; C08L 1/28
[52] U.S. Cl. ......................................... 106/197.1; 106/189
[58] Field of Search .................................. 106/189, 197.1

[56] References Cited

U.S. PATENT DOCUMENTS 4,243,802  1/1981  Landoll ...................................... 536/91

Primary Examiner—David Brunsman
Attorney, Agent, or Firm—David Edwards

[57] ABSTRACT

A clear and flexible hydrogel containing hydrophobic microdomains provides for controlled release of medicants or other agents use as a medium for chromatography. These hydrogels are produced by addition of a water insoluble hydrophobic moety containing polymer such as water insoluble hydrophobically modified hydroxyethylcellulose to a surfactant/water or ethanol/water solution where the amount of polymer and the solvent composition are sufficient to produce the hydrogel phase.

11 Claims, No Drawings

ASSOCIATIVE POLYMER HYDROGELS

This application is a continuation of application Ser. No. 07/565,704, filed Aug. 13, 1990.

FIELD OF THE INVENTION

The invention relates to hydrophobically modified polymers. In particular the invention relates to hydrogels produced with hydrophobically modified cellulose ethers.

BACKGROUND OF THE INVENTION

Londoll in U.S. Pat. Nos. 4,228,277 and 4,243,802 describes how to make and use a new viscosimetric material, i.e., hydrophobically modified cellulosic ethers. Some self associating hydrophobically modified hydroxyethylcellulases are now commercially available from Aqualon Company, a Hercules Incorporated Company, and these have found wide acceptance in coatings applications. Other self associative hydrophobically modified cellulose ethers are involved in experimental and developmental work.

Interactions of hydrophobically grafted cellulose ethers were described in the publication, "Hydrophobic Microphase Formation in Surfactant Solutions Containing an Amphiphilic Graft Copolymer," Dualeh and Steiner, *Macromolecules*, 1990, 23, 251. Association between water-insoluble $C_{12}$-grafted hydroxyethycellulose and sodium dodecylsulfate gave rise to viscoelastic solutions and hydrogels with dispersed hydrophobic microdomains. It was speculated that applications could be uncovered for these hydrogel phases.

Yet In spite of what was known concerning the utility of hydrophobically modified cellulose ethers, the full sccoe of their employment was not obvious to different artisans for different applications. Thus it remained for the present invention to expand the state of the art for the new class of materials which had come to be known as associative thickeners.

SUMMARY OF INVENTION

It is an object of the invention to provide new and useful hydrogels based on association among water insoluble hydrophobically modified cellulose ether having side chains containing at least 8 carbon atoms.

A hydrogel comprising a water insoluble hydrophobically modified hydroxyethylcellulose and a surfactant/water or ethanol/water solution separates solutes according to their hydrophobicity when used in a chromatography column.

A hydrogel comprising a relatively hydrophobic medicant or other agent in a hydrophobically modified hydroxyethylcellulose microdomain serves as a controlled release means for the medicant or agent.

DETAILED DESCRIPTION OF THE INVENTION

Functionally the hydrophobically modified cellulose ethers which produce useful hydrogels according to the invention are water insoluble polymers containing hydrophobic side chains. It was already known that these hydrophobic side chains could give associate properties such that water soluble hydrophobically modified cellulosics come to be known as associative thickeners.

It has now been discovered that a three dimensional association of side chains in water insoluble hydrophobically modified polymers gives rise to the formation of hydrophobic microdomains. A hydrophobic microdomain can be envisioned as a volume surrounded by side chains from two or more water insoluble cellulose molecules. Since like attracts like, the hydrophobic side chains attract to produce a hydrophobic phase and the cellulose ether backbones remain oriented towards the aqueous phase. Inside the volume formed by the side chains a material with some degree of hydrophobicity can be advantageously entrapped either permanently or temporarily. It is this hydrophobic phase bounded by the side chains which represents the hydrophobic microdomain found to have utility in the present invention. The hydrogel can be envisioned as a cellulosic matrix containing hydrophobic microdomains or reservoirs for storage or exchange.

These hydrophobic microdomains which are dispersed throughout a hydrophilic polymer network display the ability to absorb and release permeants in a controlled manner in proportion to permeant hydrophobicity. Discovery of the property has allowed the production of biphasic films and hydrogels having utility for chromatographic separation and controlled release. On a microscopic level these microdomains resemble surfactant micelles and have the ability to sequester solutes which are only sparingly soluble in an aqueous phase.

Water insoluble hydrophobically modified hydroxyethylcellulose and other cellulose ethers suitable for the practice of the invention are available from Aqualon, a Hercules Incorporated Company as experimental developmental or specialty products. Other hydrophobically modified and/or graft polymers and copolymers would be similarly useful for the practice of the invention provided that the molecule comprised a water soluble main chain with side chains capable of producing hydrophobic domains. The hydrophobic side chains must be present in an amount to render the molecule water insoluble. A person of ordinary skill in the art would be able to determine suitability of a particular material by testing the material in a manner as described in the example herein.

It was found that when from about 0.6 to about 1.4% by weight hydrophobically modified hydroxyethylcellulose (HMHEC) was dissolved in ethanol/water a two phase system was produced. One phase was a non-Newtonian supernatant solution containing about 0.6% polymer. The second phase was a clear and flexible hydrogel.

It was also found that HMHEC formed stiff viscoelastic hydrogels in the surfactant sodium dodecylsulfate (SDS) below the CMC (critical miscelle concentration). These hydrogels precipitated out of solution leaving some SDS and some polymer in the supernatant phase.

In summary the process of the invention involves the steps:

1. combining a surfactant/water or ethanol/water solution with a water insoluble hydrophobically modified polymer having a hydrophilic main chain and hydrophobic side chains to produce a supernatant and a two phase hydrogel comprising hydrophobic microdomains dispersed in a gel, and
2. using the hydrophobic microdomains in the hydrogel as a release or transfer site for a solute.

In detail, a process for preparation of a hydrogel for a chromatographic separation column involves the steps:

1. mixing a water-insoluble hydrophobically modified hydroxyethylcellulose with either sodium dodecylsulfate and water or ethanol and water to prepare a hydrogel, 2. separating the hydrogel from the supernatant liquid and transferring the hydrogel to a chromatographic column,
3. passing a mixture of solutes of different hydrophobicities over the hydrogel, and
4. using a carrier solvent to elute the solutes from the column in proportion to their hydrophobicity.

In detail, a process for preparation of a hydrogel for controlled release involves the steps:

1. mixing a water insoluble hydrophobically modified hydroxyethylcellulose with a relatively hydrophobic agent in a surfactant/water or ethanol/water solution to prepare a hydrogel,
2. isolating the hydrogel as a delivery medium, and
3. using the medium wherein the agent is released at a nearly constant level for the lifetime of the medium.

A particularly useful feature of the use of hydrogels as controlled release media is the discovery that zero-order (i.e., non-time-dependent) release kinetics are involved. While it is not known with certainty, it is believed that a hydrophobic drug will actually be localized within the microdomains to provide a constantly replenished saturated solution in the aqueous phase. Due to the relatively high total interfacial area between the microdomain and the gel as compared with the area between the gel and the delivery site, the replacement process would be extremely efficient wherein the aqueous phase constantly remains near saturation.

The following examples illustrate the practice of the invention without being limiting. The invention has industrial applicability in the analytical field and in any field requiring controlled release such as medicine-pharmacy, personal care, agriculture, cosmetic, fragrance, etc.

The following procedures and/or functionally equivalent procedures were employed in the examples which follow:

For fluorescence testing all solutions were made up by weight in distilled water saturated with recrystallized pyrene ($3 \times 10^{-7}$M pyrene) and stirred for an hour. Steady state fluorescence spectra of the pyrene in the solution excited at 310 nm. were obtained on a Spex Fluprolog-2 model 112A fluorescence spectrometer (Spex Industries, Inc., Edison, N.J.). All spectral characteristics of the pyrene remained constant for at least 24 hours after solution preparation. For samples in which both a gel and supernatant formed, this indicated that the pyrene had equilibrated between the two phases.

Conductivity measurements on the polymer solutions were performed on a conductance-resistance meter (Yellow Springs Instrument Co. Inc. Yellow Springs, Ohio 45387) using a probe with a cell constant of 1.0 cm$^{-1}$. In cases where the sample comprised both a supernatant solution and a hydrogel, only the supernatant conductivity was measured.

Surface tensions of the solutions were measured using a Wihelmy plate-type surface tensiometer.

Viscosities were measured using a Brookfield cone-and-plate viscometer with a constant temperature (25±0.1° C. circulating) water bath or using a Ubbelohde viscometer, in which the time for a liquid to flow through a capillary under gravity is measured. The procedure was repeated three times on each solution with an accuracy greater than ±0.5%.

Dynamic mechanical measurements of the gels were performed using a cone and plate Instron 3250 Rotary Rheometer operating in the oscillating mode. The phase angle was measured with a Solartron frequency response analyzer to obtain the storage and loss moduli of the gels.

Differential scanning calorimetry (DSC) studies were conducted using a DuPont Instruments TA 2100 Thermal Analyzer and 910 DSC.

Unless otherwise specified all preparations were on a weight/weight or volume/volume basis.

EXAMPLE 1

Surfactant solutions were prepared with sodium dodecyl sulfate (SDS) 99% pure available from Fluka and distilled water and varying amounts of water insoluble hydrophobically modified hydroxyethylcellulose (HMHEC) containing $C_{12}$ side chains with 1.3% hydrophobic substitution (available from Aqualon) and these were tested for solubility and/or phase separation.

It was observed that on addition of 0.15% (W/W) HMHEC to distilled water that the polymer settled in the form of individual globules. In the presence of up to $1 \times 10^{-3}$M SDS it was observed that some of the polymer formed a macroscopic layer on the surface. At higher SOS concentrations, two distinct macroscopic phases were formed. Conductivity, viscosity and fluorescence measurements of the clear supernatant phase revealed that most of the surfactant (up to $8 \times 10^{-3}$M) and a small amount of the polymer were present. The polymer-rich hydrogels obtained with the higher level of surfactant (up to $8 \times 10^{-3}$M) were clear and flexible hydrogels which took the shape of their container. These hydrogels did not swell further and were not dispersible in pure water.

At surfactant levels above the critical miscelle concentration (CMC) of about $8 \times 10^{-3}$M, the hydrogel no longer formed and the polymer was solubilized in the aqueous phase. Thus it was discovered that the region for hydrogel formation with SDS for this particular hydrophobe and substitution level and polymer molecular weight was between $1 \times 10^{-3}$M and $8 \times 10^{-3}$M, a region just below the CMC.

EXAMPLE 2

Example 1 was repeated except that sodium oleate was used as the surfactant and HMHEC or unmodified HEC was added. The CMC for this surfactant was 0.042% (W/V).

Addition of water-insoluble HMHEC to varying concentrations of sodium oleate in water gave rise to viscosity profiles which exhibited a peak at or near the CMC but dropped to baseline values above and below this region. The viscosity peak is believed to represent intermolecular entanglements connected with microdomains.

Addition of water-soluble HEC to varying concentrations of sodium oleate in water gave rise to a flat viscosity profile signifying that the $C_{12}$ side chains were responsible for the viscosification in the region of the CMC for sodium oleate.

This example illustrates that microdomains useful for entrapment of partially hydrophobic solutes or medicants can be produced in liquid form in addition to the hydrogel form of Example 1.

EXAMPLE 3

Hydrogels produced in Example 1 were further examined under oscillatory shear and found to be stable. The hydrophobic microdomains remained intact on drying and were found to be amorphous. The microdomains in the hydrogels were able to solubilize pyrene, water insoluble dyes and other small solutes and yet remain stable and suitable for controlled release or chromatographic separation.

In addition to pyrene the formation of hydrophobic domains was further confirmed by using the fluorescence probe tris(2-2 bipyridine) ruthenium (II) chloride (AESAR, 892 Lafayette Road, P.O. Box 1087, Seabrook, N.H. 03874-1087), emission wavelength maximum in SDS of 628 nm (excitation at 453 nm). The quencher was 9-methylanthracene. When the probe and quencher were injected prior to formation of the hydrogel, a small but reproducible (to ±0.5%) amount of the probe always remained in the supernatant. If the probe and quencher were introduced after the hydrogel had formed, they remained in the supernatant.

EXAMPLE 4

Hydrogels are produced as in Example 1 except that SDS is partially or totally replaced with polyoxyethylene (PEO) lauryl ether having a lower CMC. As expected, the concentration range of total surfactant at which the hydrogel is produced decreases in proportion to the amount of SDS being replaced. In all cases the formation region for the hydrogel will be proportional to the viscosification region observed in Example 2, i.e., near and below the CMC of the mixture. Hydrogels produced with or without SDS will all be suitable for analytical or release uses.

EXAMPLE 5

Samples of water insoluble hydrophobically modified hydroxyethylcellulose (HMHEC) with ranges of molecular weight (50,000 to 1,000,000), hydrophobic moieties ($C_8$ to $C_{20}$) and hydrophobe content (0.8 to 1.5 weight percent) were tested in comparison to hydroxyethylcellulose (HEC) of comparable molecular weight (50,000 to 1,000,000) but without hydrophobe substitution. All sample materials were supplied by the Aqualon Company.

Samples of both HMHEC and control HEC were placed in ethanol/water solutions and surface tension and viscosity measurements were run on the liquid phases. Where a hydrogel formed with HMHEC, the gel was characterized by DSC, storage and loss moduli and steady state fluorescence.

Ethanol/water was an appropriate solvent for the HMHEC because it allowed non-hydrogen bonding species to become solubilized. Four regions of behavior were identified over the range 0.1–1.4% polymer in HMHEC/ethanol/water solutions. Below 0.3% polymer the one phase system exhibited Newtonian behavior ever the shear rate range $11.5 < w < 230$ $\sec^{-1}$. At 0.3% polymer a step increase in surface tension appeared which reflected an increased tendency for the polymer to remain in the bulk phase. Between 0.3% and 0.6% HMHEC the solutions were one-phase and non-Newtonian. This non-Newtonian behavior did not change over a period of four days which indicated that the intermolecular interactions giving rise to the non-Newtonian behavior were stable as well. At 0.6% HMHEC the polymer solutions became saturated and at 0.6% to 1.4% polymer two distinct macroscopic phases formed. There was a non-Newtonian supernatant solution containing about 0.6% polymer; and a clear, one-piece, flexible gel which took the shape of the container and retained solvent even under moderate applied pressure. The hydrogel and the supernatant had equal volumes. Above 1.4% polymer the supernatant became highly non-homogeneous. By comparison no similar phase transition was observed when HEC was added in the same way, thereby confirming that the hydrophobic side chains were responsible for the new and useful hydrogels produced according to the invention.

It was observed that the ethanol/water (w/w) ratio had to comprise about 44% ethanol in order to allow production of hydrogels which were demonstrated to be optimal with respect to their bulk properties and for chromatography and controlled release applications. For convenience, equal volume mixtures of ethanol and water can be used for large scale hydrogel production for applications in chromatographic separations and controlled release.

EXAMPLE 6

Hydrogels produced in Example 5 were dried in air at room temperature and then immersed in (1) pure water or (2) 50% (v/v) ethanol/water or (3) ethanol. In (1) or (2) the HMHEC hydrogels swelled isotropically to their original volumes without dispersing further, but in (3) the clear hydrogels did not dissolve or change shape for as long as five days. This illustrated that the hydrophobic microdomains were completely segregated from the bulk material of the HMHEC hydrogel and were stable to the drying process. DSC further confirmed the amorphous rather than crystalline structure of these hydrogels. This is significant since only amorphous microdomains or aggregates would be capable of incorporation of foreign material to provide the utility demonstrated for chromatographic exchange and for the controlled release of a relatively hydrophobic medicant or other agent.

EXAMPLE 7

A hydrogel as produced in Examples 1, 4 or 5 is dried and placed in a chromatographic column. A mixture of benzoic acid derivatives is added to the hydrogel and absorbed therein. As the solute mixture is eluted with cyclohexane it will be observed that the derivatives are fractionated by increasing hydrophobicity.

EXAMPLE 8

Dried hydrogels as produced in Examples 1, 4 or 5 are reconstituted with a solution containing hydrophobic agents so that they are incorporated into the hydrophobic microdomains of the hydrogel.

EXAMPLE 9

Clear hydrogels as produced in Example 1, 4, 5 or 8 to include theophylline, a relatively hydrophobic medicant, are prepared. The hydrogels combining the medicant are placed in distilled water which is changed at half hour intervals over an eight hour period and a chemical test is performed on the water in each instance for theophylline. In all cases the amount of theophylline is within experimental error for a demonstration of zero order release.

EXAMPLE 10

A water soluble hydrophobically modified hydroxyethylcellulose with a degree of hydrophobic substitution below 0.8 weight percent is added to either SDS/water or ethanol/water solution. No hydrogel or biphase formation is observed.

What is claimed is:

1. A clear and flexible hydrogel comprising a water-insoluble hydrophobically modified hydroxyethylcellulose polymer with a molecular weight of at least 50,000 having a degree of hydrophobic substitution of at least 0.8% by weight with hydrophobic moieties having at least 8 carbon atoms, where the hydrogel is formed in a surfactant aqueous solution below the critical micelle concentration of the surfactant or in an ethanol aqueous solution and is characterized by a two phase structure of a swollen aqueous gel phase with stable hydrophobic microdomains dispersed throughout the gel phase which microdomains are composed only of hydrophobic moieties from the polymer and surfactant or ethanol.

2. The hydrogel of claim 1 where the hydrophobic moieties contain 10 to 16 carbon atoms.

3. The hydrogel of claim 2 where the degree of hydrophobic substitution is 1.2% or higher.

4. The hydrogel of claim 3 where the hydrophobic moety contains 12 carbon atoms.

5. The hydrogel of claim 1 which is formed in an ethanol/water solution.

6. The hydrogel of claim 1 wherein the microdomains are intermolecular aggregates composed of hydrophobic side chains pendant to the hydrophobically modified hydroxyethylcellulose polymer.

7. A process for producing a swollen gel of a hydrophobically modified cellulose ether in water, characterized in that the process produces clear and flexible hydrogels by the steps of (a) preparing solutions of sodium dodecyl sulfate (SDS) and 50,000 to 1,000,000 molecular weight hydrophobically modified hydroxyethylcellulose (HMHEC) with 0.8 to 1.5 weight percent hydrophobic substitution by 8 to 20 carbon atom moieties, (b) mixing solutions of SDS and HMHEC to prepare a mixture in the concentration range $1 \times 10^{-3}$M to $8 \times 10^{-3}$M SDS to produce a clear and flexible hydrogel, and (c) separating the hydrogel in an amorphous form such that the hydrogel comprises hydrophobic microdomains.

8. The process of claim 7, further characterized in that the HMHEC is hydrophobically substituted with from 1.2 to 1.5 weight percent with dodecyl or nonylphenyl.

9. A process for producing a swollen gel of a hydrophobically modified cellulose ether in water, characterized in that the process produces a clear and flexible hydrogel by mixing an ethanol/water solution containing about 44% by weight ethanol with from 0.6 to about 1.4% by weight hydrophobically modified hydroxyethylcellulose (HMHEC) with 0.8 to 1.5 weight percent hydrophobic substitution.

10. The process of claim 9, further characterized in that the hydrogel is separated and dried.

11. The process of claim 10, further characterized in that the HMHEC is substituted with from 1.2 to 1.5% by weight of dodecyl or nonylphenyl.

* * * * *

UNITED STATES PATENT AND TRADEMARK OFFICE
CERTIFICATE OF CORRECTION

PATENT NO. : 5,512,091
DATED : April 30, 1996
INVENTOR(S) : Carol A. Steiner

It is certified that error appears in the above-indentified patent and that said Letters Patent is hereby corrected as shown below:

Column 7, line 9, replace "moety" with --moiety--.

Column 8, line 3, replace subscript "3" with superscript --3--.

Signed and Sealed this

Twenty-first Day of January, 1997

Attest:

BRUCE LEHMAN

*Attesting Officer*   Commissioner of Patents and Trademarks